United States Patent [19]

Lowther

[11] Patent Number: 4,994,742
[45] Date of Patent: Feb. 19, 1991

[54] HALL EFFECT DEVICE AND MAGNETIC COIL CIRCUITS FOR MAGNETIC FIELD DETECTION

[75] Inventor: Frank E. Lowther, Plano, Tex.

[73] Assignee: Atlantic Richfield Company, Los Angeles, Calif.

[21] Appl. No.: 403,548

[22] Filed: Sep. 6, 1989

Related U.S. Application Data

[63] Continuation-in-part of Ser. No. 262,372, Oct. 25, 1988, Pat. No. 4,945,306.

[51] Int. Cl.$^5$ .................. G01R 33/02; G01R 33/06; H03K 17/90
[52] U.S. Cl. .................................... 324/251; 307/309; 324/235; 324/258
[58] Field of Search ............. 324/235, 240, 251, 258, 324/117 H, 119; 307/309; 338/32 H; 73/DIG. 3

[56] References Cited

U.S. PATENT DOCUMENTS 2,585,707  2/1952  Warner ................. 324/119

FOREIGN PATENT DOCUMENTS 124528  2/1959  U.S.S.R. ................. 324/251
890411  2/1962  United Kingdom ......... 324/251

Primary Examiner—Gerard R. Strecker
Attorney, Agent, or Firm—Michael E. Martin

[57] ABSTRACT

Magnetic field sensing circuits including wire coils and Hall effect devices are provided which produce high-gain output for a relatively low change in perceived field intensity. Series connected plural Hall effect devices are connected to the coil and include amplifier and integrator circuits interposed at selected points between Hall effect devices to modify the output signal gain and passband. The circuits may include diode and capacitance elements to modify the circuit output signal.

2 Claims, 3 Drawing Sheets

HALL EFFECT DEVICE AND MAGNETIC COIL CIRCUITS FOR MAGNETIC FIELD DETECTION

CROSS REFERENCE TO RELATED APPLICATION

This application is a continuation-in-part of U.S. Pat. Application Ser. No. 07/262,372 filed Oct. 25, 1988 now U.S. Pat. No. 4,945,306 issued July 31, 1990.

BACKGROUND OF THE INVENTION

1. Field of the Invention

The present invention pertains to improved electrical circuits for detecting perceived changes in magnetic fields and which include one or more Hall effect devices in circuit with a magnetic coil.

2. Background

The above-referenced patent application, which is incorporated herein by reference, describes a unique circuit wherein a magnetic coil and a Hall effect device are exposed to a magnetic field and are in circuit with each other to provide an amplified output signal. Such a device is advantageously used in detecting perceived changes in a magnetic field such as sensing cracks and other magnetic anomalies in structures. However, the combination of a magnetic coil, which is capable of generating an output current in response to a change in a magnetic field, in circuit with a Hall effect device, which is exposed to the same changing magnetic field, and further in combination with an integrating circuit is capable of being utilized in other applications wherein relatively low intensity magnetic fields are required to be sensed. For example, a circuit including multiple Hall effect devices with a magnetic coil and an integrator circuit provides a useful switch circuit thanks to the high amplification characteristics of the combination of the coil and the multiple Hall effect devices. The gain of such a circuit is particularly advantageous for applications such as in conjunction with proximity sensing devices and magnetic domain systems. Certain other applications which present problems for prior art magnetic field sensing circuits include fast and slow changing magnetic fields or changing magnetic fields imposed on substantially constant magnetic fields. These applications also find solutions by the use of certain ones of the circuits of the present invention.

SUMMARY OF THE INVENTION

The present invention provides certain improved circuits which include combinations of Hall effect devices with a magnetic coil and amplifier or integrator circuits and which are well suited for applications wherein low-level magnetic fields or magnetic fields with low levels of change may be sensed and certain switching or detecting functions carried out.

In accordance with one embodiment of the present invention, multiple Hall effect devices are arranged in circuit with each other and with a magnetic coil in series relationship and are adapted to be exposed to a magnetic field wherein the signal amplification provided by the circuit is of a particularly high order. Accordingly, the output signal per unit of incident magnetic flux is substantial even for fields of minimal magnetic intensity.

In accordance with another aspect of the present invention, there are provided circuits which include a magnetic coil, one or more Hall effect devices and integrating circuits interposed therein in selected positions in the circuit to provide a selected output signal magnitude and for filtering noise signals sensed by the circuit. The integrator circuit may have a band pass characteristic which is selected to pass the "fastest" changing magnetic field that is expected and to avoid giving an output signal where lower frequency outputs or noise are sensed.

Still further, the present invention contemplates the provision of circuits which include coil and Hall effect devices which are arranged to provide an output signal only after sensing a predetermined number or magnitude of magnetic anomalies. The coil-Hall effect device circuits may also be arranged in pairs which are staggered or squinted to look at different areas in the field of view of the entire circuit. The circuit pairs may be connected to eliminate a bias field imposed on the circuit, in a bridge arrangement to be utilized, for example, to measure cross field component differences, or to indicate the direction of field intensity changes with or without eliminating background or steady state field intensity.

The above-noted advantages and features of the present invention together with other superior aspects thereof will be further appreciated by those skilled in the art upon reading the detailed description which follows in conjunction with the drawing.

DESCRIPTION OF PREFERRED EMBODIMENTS

Figure 1:
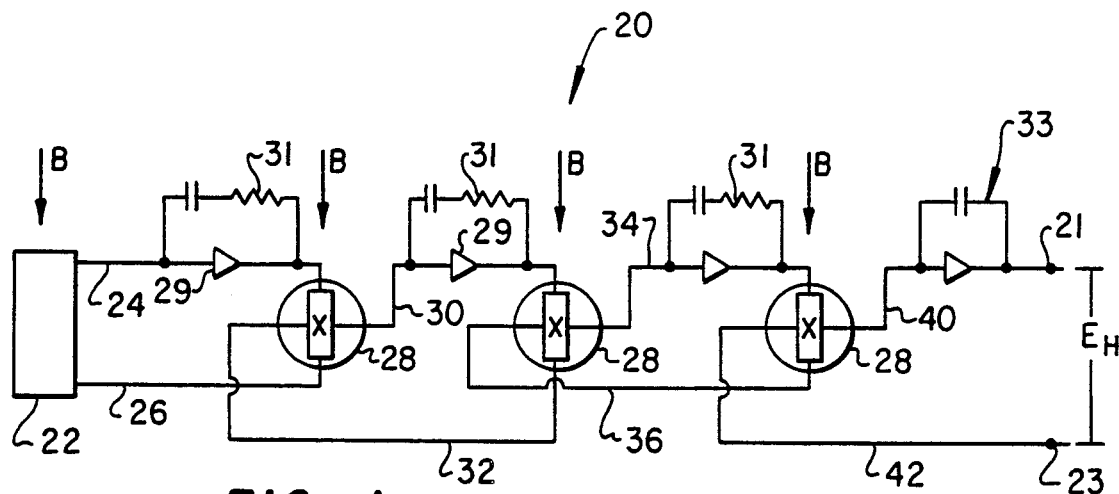
FIG. 1 is schematic diagram of one preferred embodiment of a circuit in accordance with the present invention.

In the description which follows, like elements are marked throughout with the same reference numerals where appropriate. The diagrams are adapted to show conventional circuit elements by the use of accepted symbols for such elements.

Referring to FIG. 1, there is illustrated a circuit 20 which is adapted to be exposed to a magnetic field B and includes a wire coil or sensing element 22 having conductors 24 and 26 connected thereto and to a Hall effect element or device 28. In other words the bias current terminals of the Hall effect device 28 are connected to the conductors 24 and 26 and the voltage output terminals of the Hall effect device are connected to conductors 30 and 32. The conductors 30 and 32 are connected to a second Hall effect device 28 at its bias current input terminals and the Hall effect voltage (output voltage) terminals of the second Hall effect device 28 are connected to conductors 34 and 36. The conductors 34 and 36 are, as illustrated, connected to the bias current input terminals of a third Hall effect device 28.

The third Hall effect device 28 has its voltage output terminals connected to conductors 40 and 42 which provide the Hall effect output voltage ($E_H$) of the circuit 20, as indicated. The circuit 20 of FIG. 1 may include suitable amplifiers interposed between the respective Hall effect elements 28, which amplifiers are indicated by the numeral 29, respectively. Still further, suitable filter circuits 31 may also be interposed between each of the Hall effect devices 28 and between the first Hall effect device 28 and the coil 22. Still further, an integrator circuit 33 may be interposed between the output terminals 21 and 23 of the circuit 20 and the third Hall effect device 28.

The output voltage $E_H$ of the circuit 20 may be expressed according to the following relationship:

$$E_H = K_o \left[ \frac{K^N \cdot B^{N+1}}{N+1} \right] \quad (1)$$

where:
  $K_o$ is a coil constant;
  K is a constant related to the characteristics of the Hall effect devices;
  N is the number of Hall effect devices or "stages"; and
  B is the magnetic field intensity.

Accordingly, minute changes in a magnetic field having an intensity B may be more easily sensed to provide a useful output signal $E_H$ with multiple Hall devices arranged per the circuit of FIG. 1. The gain in the output voltage as indicated by the above-noted relationship per unit of incident magnetic flux is substantial. For example, for the circuit 20 of FIG. 1 the output voltage ($E_H$) is proportional to the fourth power of the magnetic field intensity and the third power of the sensitivity constant (K) of the Hall effect device.

Figure 7:
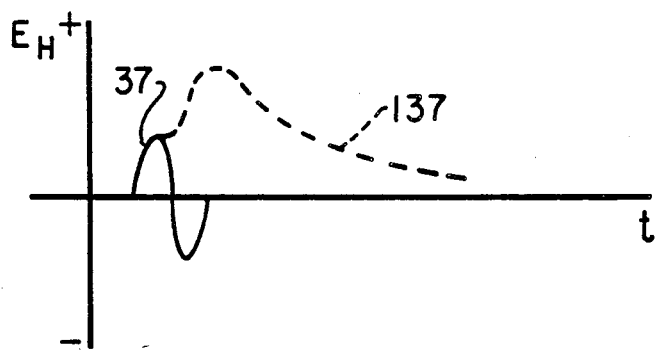
FIG. 7 is a diagram of the output signal of certain ones of the circuits of the present invention.

The threshold of the intensity of the magnetic field B can be considerably lower than otherwise is possible for utilization of a coil and Hall effect circuit. Obviously, the limitations of available space for a particular application would dictate the number of Hall effect elements which could be exposed to the magnetic field being sensed. The circuit of FIG. 1, including more or less numbers of Hall effect devices connected in series, is particularly useful as a switch. Signals of a predetermined bandwidth and comprising "noise" may be omitted by utilization of the amplifier filter circuits 29 and 31 as well as utilization of the integrator circuit 33. Moreover, in applications of circuits in accordance with the present invention for sensing magnetic anomalies such as in the application for detecting cracks in metal structures, the output voltage $E_H$ is in the form of a generally sinusoidal waveform having a first phase which is always of a positive nature. Since the relationship in equation (1) is derived by integrating over a period of time the product of the magnetic field intensity and the change in the magnetic field intensity as a function of time, the positive or negative sign of the magnetic field with respect to the circuit sensing the field is of no consequence, the voltage output signal will always, on the first phase of its cycle, be indicated as a positive quantity. This relationship will help eliminate at least certain categories of interference or so-called "noise" signals in applications of the circuits of the present invention to such uses as crack or other magnetic anomaly detectors. FIG. 7 illustrates a typical output signal $E_H$ for the circuit of FIG. 2 for example, as indicated by the generally sinusoidal waveform 37. As mentioned above, the first half-wave portion of this waveform is of a positive nature with respect to the polarity of the output signal. The diagram of FIG. 7 is a plot of the voltage output signal ($E_H$) of the circuit as a function of time (t).

Figure 2:
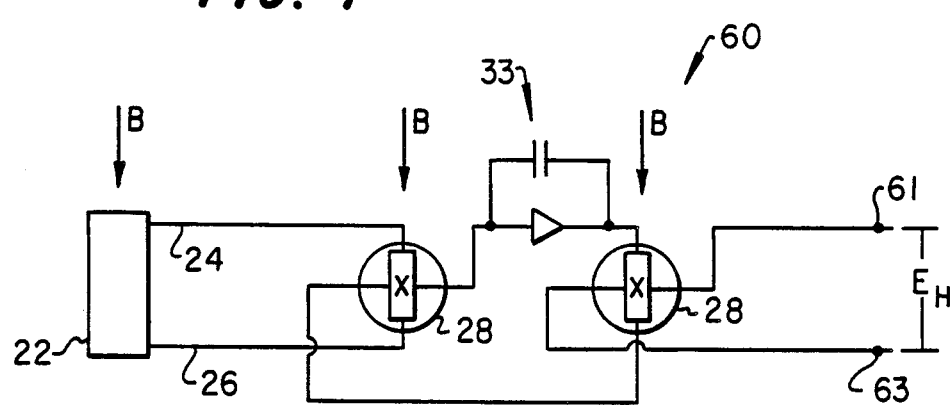
FIG. 2 is a schematic diagram of another embodiment of a circuit in accordance with the present invention.
Figure 3:
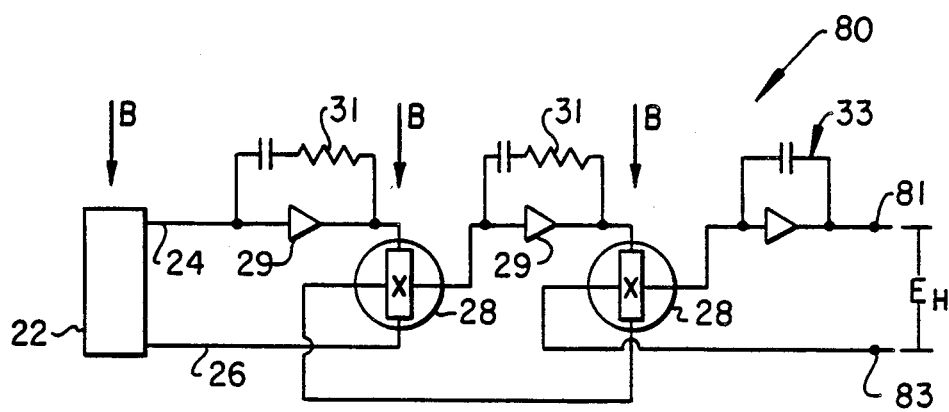
FIG. 3 is a schematic diagram of a third embodiment of a circuit in accordance with the present invention.

Referring now to FIG. 2, there is illustrated a circuit generally designated by the numeral 60 having a wire coil 22 connected to a Hall effect device 28 in a manner similar to the circuit of FIG. 1 and which may or may not include an amplifier interposed in the conductor 24. The first Hall effect device 28 is connected to a second Hall effect device 28 in the same manner as the configuration of FIG. 1, however, an integrator circuit 33 is interposed between the two Hall effect devices 28 and the second Hall effect device is connected directly to output terminals 61, 63. FIG. 3 illustrates a circuit 80, similar to FIG. 2, and including suitable amplifier and noise cancellation circuits 29 and 31 and wherein the integrator circuit 33 is disposed at the output of the last stage Hall effect device 28. In the general case of a circuit wherein N Hall effect devices are connected in series as shown in FIGS. 1, 2 and 3 and the integrator circuit 33 is interposed between the first stage Hall effect device and the subsequent stages, the output voltage signal $E_H$ is dependent on the relationship, $$E_H \propto \frac{B^{N+1}}{1} \quad (2)$$

On the other hand, for the arrangement illustrated in FIG. 1 or FIG. 3 wherein the integrator circuit 33 is interposed in the overall circuit after the last Hall effect device 28, the output voltage signal $E_H$ is according to the relationship, $$E_H \propto \left( \frac{1}{N+1} \right) \cdot B^{N+1} \quad (3)$$

As will be seen from the foregoing proportionality relationships of the circuit output voltage signal to the location of the integrator circuit, the arrangement of FIG. 2 is preferred as the output voltage is greater by a factor of $(N+1)/2$. The effect of scaling constants and interstage amplifiers have been omitted from these proportionality relationships.

The placement of the integrator circuit in a circuit such as one of those illustrated in FIGS. 1 through 3 as well as the operational characteristics of the integrator circuit may or may not be important depending on the application of the circuit. For example, wherein primarily a switching action is desired in response to a change in the intensity of the magnetic field B, the magnitude of the intensity change may not be important but just the fact that a change greater than some threshold value has taken place. In such a case, it may not be necessary to include an integrator circuit at all in one of the circuits of FIGS. 1 through 3, for example. Preferably, the integrator band pass is selected to pass the fastest changing flux signal that is expected and to not pass lower frequency signals and so-called noise. Moreover, for relatively slowly changing flux or magnetic field intensity, the integrator circuit may be desired whereas for rapid changes or pulse-type changes in field intensity, it may be preferable to not place an integrator circuit in the field detection circuit.

In many applications wherein a circuit in accordance with the present invention would be useful, a steady or non-changing or so-called DC magnetic field would be incident on the sensitive portions of the circuit in addition to a rapidly-changing field portion. The signal that is desired to be sensed may be represented by this change in field intensity. The steady state magnetic field component most frequently represents an unwanted signal source that can induce undesirable side effects in the sensing circuit. Amplifiers in the circuit may undesirably change the field signal and hysteresis effects may limit sensitivity to the changing field intensity. In some applications a blocking capacitor may effectively block the unwanted portion of the signal. However, for certain other applications including applications of Hall effect devices to computer memory circuits such as magnetic domain systems, the size of the blocking capacitor may become impractically large.

Figure 4:
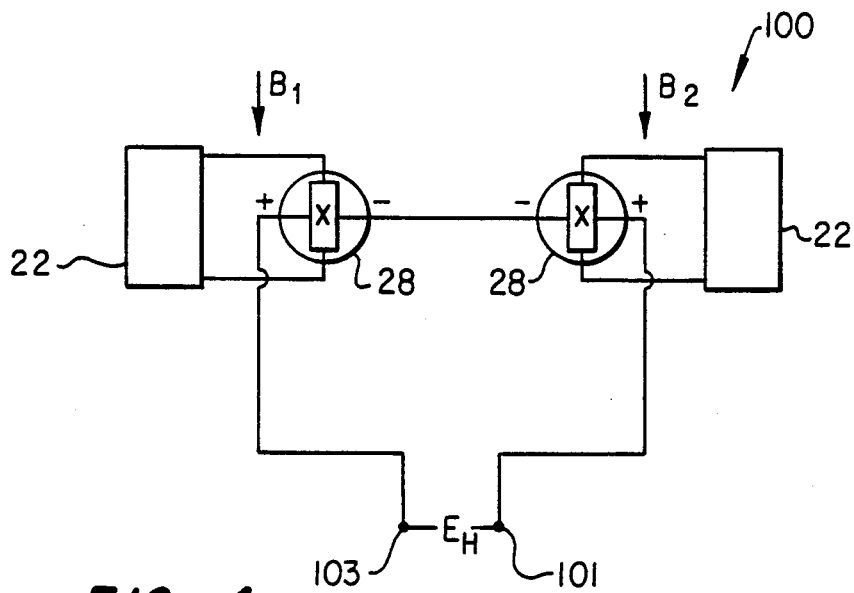
FIG. 4 is a schematic diagram of a fourth embodiment of a circuit in accordance with the present invention.

FIG. 4 illustrates a circuit 100 in one of the simpler forms for applications such as those discussed above. In the circuit of FIG. 4, two coils 22 are each connected to a Hall effect device 28 in such a way that during steady state field exposure to both circuits, the output signal of each Hall effect device-coil combination cancels the output signal of the other, thanks to the connection illustrated. However, if one of the Hall effect device-coil circuit combinations senses a field intensity $B_2$ which is greater than $B_1$, an output signal would appear on the circuit output terminals 101, 103. In the circuit illustrated in FIG. 4, the sensor pairs, comprising a coil 22 and a Hall effect device 28, eliminate the effects of a steady state field bias imposed on both sensors.

Figure 5:
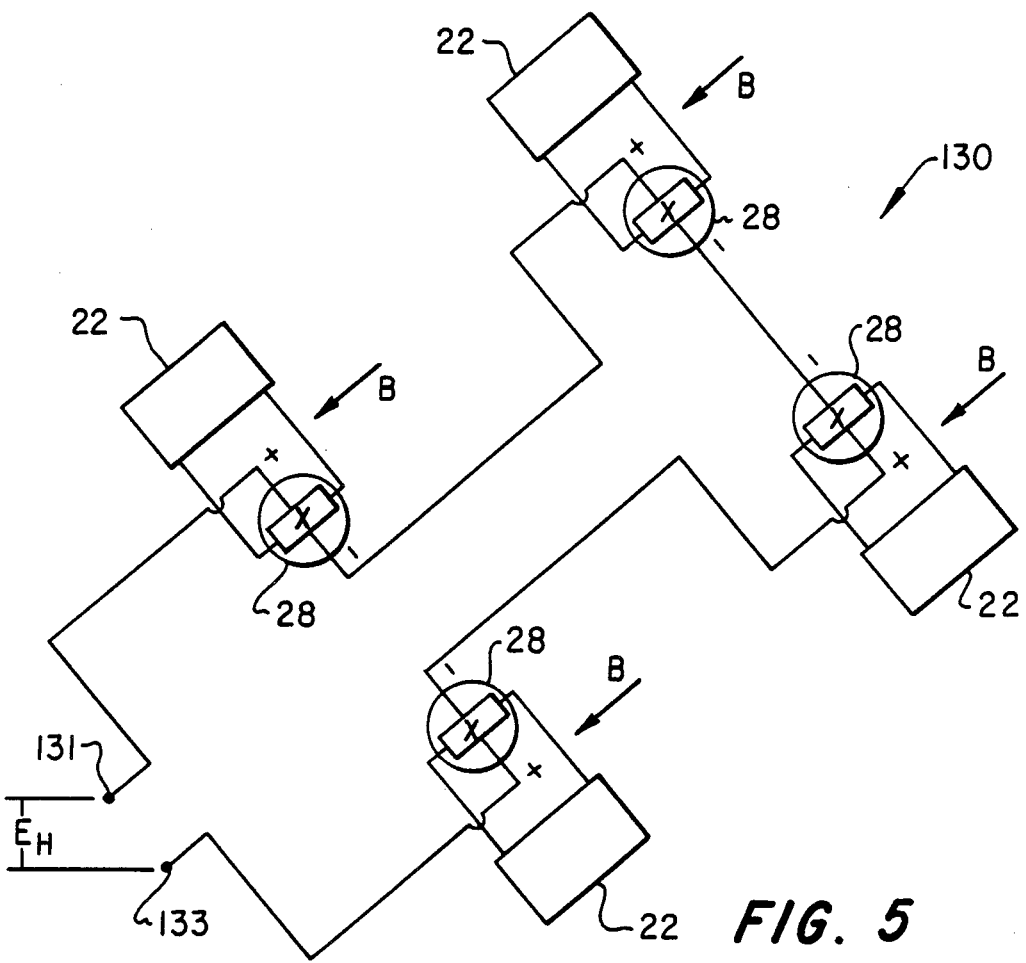
FIG. 5 is a diagram of another circuit of the present invention.

FIG. 5 illustrates yet another circuit, generally designated by the numeral 130, which comprises a bridge arrangement as illustrated with respect to each of the coil 22 and Hall effect device 28 component circuits and which could be utilized to measure differences across a magnetic field, depending on the configuration of the field and the physical arrangement of each of the coil-Hall device component circuits. The four individual coil-Hall device circuits could be series connected, as shown, or connected in an alternate series, parallel or series-parallel arrangement.

Figure 6:
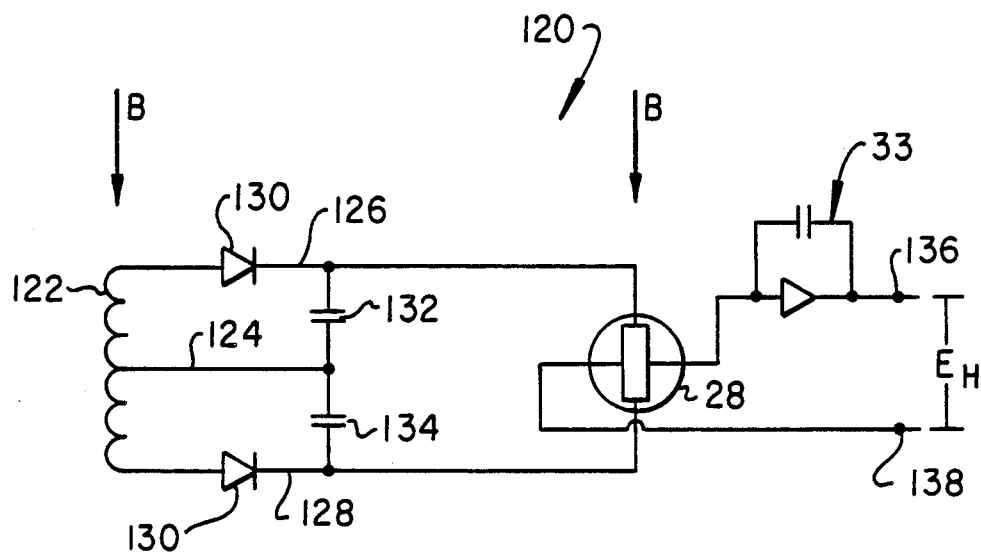
FIG. 6 is a diagram of a sixth embodiment of a circuit of the present invention.

Referring now to FIG. 6, there illustrated yet another circuit in accordance with the present invention which has advantageous characteristics for certain applications, such as when it is desired to sense only a series of magnetic anomalies or events which occur close together in time as regards the sensing characteristics of the circuit. The circuit of FIG. 6 is generally designated by the numeral 120 and includes a coil 122 having a configuration which provides for a center or adjustable conductor 124 intermediate the conductors 126 and 128. The circuit 120 may also include diodes 130 interposed in the respective conductors 126 and 128. The diodes 130 alone are operable to provide a positive only half-wave voltage output signal ($E_H$) for the circuit 120. The conductors 126 and 128 are interconnected as illustrated with the adjustable or center tap conductor 124 through capacitances 132 and 134. The conductors 126 and 128 are also connected to the bias current terminals of a Hall effect device 28 whose output conductors are connected to circuit output terminals 136 and 138. An integrating circuit 33 may be interposed in the circuit 120 as illustrated.

Referring again to FIG. 7, the circuit 120 has an output signal characteristic indicated by the dotted line 137 which results from the charge buildup in the capacitances 132 and 134 and the rectification of the sinusoidal output waveform 37 into a so-called positive only output signal. The circuit 120 may be advantageous for applications wherein the anomaly being sensed is such that only several anomalies of the same type and closely spaced from each other are desired to be detected.

The unique combinations of the present invention comprise magnetic field sensing devices of improved sensitivity and noise rejection capability which provide circuits which may be utilized in many applications including magnetic anomaly detectors, magnetic domain systems and various switching applications. For purposes of the discussion in this specification the term "change in magnetic field intensity" shall include conditions wherein the actual field intensity changes as well as conditions wherein the field intensity as perceived by the sensing circuit changes. Although preferred embodiments have been described herein in some detail, those skilled in the art will recognize that certain substitutions and modifications may be made to the invention defined in the appended claims without departing from the scope and spirit thereof.

What is claimed is:

1. A circuit for detecting perceived changes in the intensity of a magnetic field comprising:

a coil adapted to be disposed in said magnetic field and including conductor means for conducting a current in response to a change in the intensity of said magnetic field as sensed by said coil;

a Hall effect device adapted to be disposed in said magnetic field with said coil and including conductor means for imposing a bias current thereon and connected to the conductor means of said coil for receiving as a bias current the current output by said coil in response to said change in said magnetic field;

output conductor means connected to said Hall effect device for producing a voltage signal which is proportional to said perceived change in said magnetic field;

a circuit element interposed in at least one of said conductor means of said coil for converting a generally sinusoidal output signal of said circuit to a generally half-wave output signal at said output conductor means; and said coil includes an intermediate tap comprising a conductor which is interconnected with said conductor means of said coil by respective capacitances which are dischargeable into said Hall effect device to provide a time-delayed voltage output signal at said output conductor means.

2. The circuit set forth in claim 1 wherein said coil and said Hall effect device are arranged to sense said magnetic field such that said half-wave signal has a positive polarity characteristic.

* * * * *